United States Patent [19]
Sullivan

[11] Patent Number: 5,292,929
[45] Date of Patent: Mar. 8, 1994

[54] ASYMMETRIC SYNTHESIS OF CHIRAL SECONDARY ALCOHOLS

[75] Inventor: Jeffrey M. Sullivan, Longmont, Colo.

[73] Assignee: Boulder Scientific Company, Mead, Colo.

[21] Appl. No.: 51,994

[22] Filed: Apr. 26, 1993

[51] Int. Cl.$^5$ .............................................. C07C 69/02
[52] U.S. Cl. ..................................... 560/231; 560/236
[58] Field of Search ................................ 560/231, 236

[56] References Cited

U.S. PATENT DOCUMENTS

| | | | |
|---|---|---|---|
| 4,095,038 | 6/1978 | Boguth et al. | 560/231 X |
| 4,314,072 | 2/1982 | Syrier | 560/231 X |
| 5,041,613 | 8/1991 | McCombs | 560/231 X |

*Primary Examiner*—Arthur C. Prescott
*Attorney, Agent, or Firm*—Edward S. Irons

[57] ABSTRACT

A process for producing (R)-2-hydroxy-6-haloalkane is disclosed. In the first step, a cyclic alkanol is photohalogenated. In the second step, the photohalogenation product is reacted with a chiral catalyst and dialkyl zinc to produce (R)-2-hydroxy-6-haloalkane.

5 Claims, No Drawings

ASYMMETRIC SYNTHESIS OF CHIRAL SECONDARY ALCOHOLS

FIELD OF THE INVENTION

This invention relates to the synthesis of chiral secondary alcohols and to derivatives thereof.

BACKGROUND OF THE INVENTION

Existing processes for the synthesis of chiral secondary alcohols and derivatives thereof require multiple steps and hence suffer from low yields. Various known processes also require expensive chiral directors such as pinanediol or a chirally active starting material such as an α-halo boronic ester. See, e.g., Brown, et al., *Tetrahedron* 37:3547–3587 (1981 (review); Matteson, et al., *J. Am Chem. Soc.* 108:810–819 (1986); Matteson, D.S., *Acc. Chem. Res.* 21:294–300 (1988); and Matteson, D.S. *Chem. Rev.* 89:1535–1551 (1989). Soai, et al., *J. Org. Chem.* 56:4264–4268 (1991) describes the synthesis of optically active secondary aliphatic and aromatic alcohols by the chiral N,N-diaklynorephedrine-catalyzed enantioselective addition of dialkyl zincs to aldehydes.

SUMMARY OF THE INVENTION

The two step process of the invention comprises photohalogenation of a cyclic alkanol to produce a halogenated aldehyde for reaction with dialkyl zinc and a chirally active catalyst to produce a chiral secondary alcohol.

DETAILED DESCRIPTION OF THE INVENTION

The photohalogenation step of the invention is illustrated by Equation I:

EQUATION I

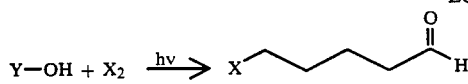

in which Y is a cyclic alkyl radical having from 5 to 10 carbon atoms and X is a halogen, Y-OH is preferably cyclopentanol or cyclohexanol, X is preferably chlorine or bromine. See generally Deno, et al., *J. Org. Chem.* 39(4):520 ( 1974)

The haloaldehyde product is reacted with a dialkyl zinc in the presence of a chirally active catalyst to produce a chiral secondary alcohol as depicted by Equation II:

EQUATION II

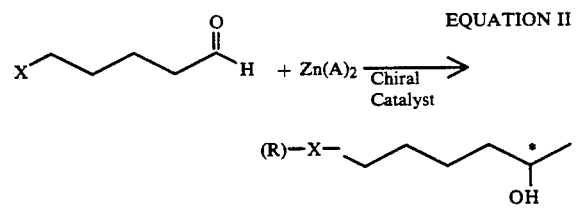

in which X is the halogen preferably chlorine or bromine in the photohalogenation product, and A is an alkyl group having from one to five carbon atoms. Dimethyl or diethyl zinc is preferred.

Various known chirally active catalysts may be utilized. Both (1S,2R)- and (1R,2S)-N,N dialkylnorephedrine are suitable. The alkyl substituents may have from 1 to 8 carbon atoms. Preferably the alkyl groups have two to four carbon atoms. 1R,2S-(-)-N,N-dibutylnorephedrine (DBNE) is preferred. See Soai, supra.

EXAMPLE

Reaction Step 1

To a nitrogen-purged 2000=mL 3-neck round-bottom pyrex glass flask fitted with a stirrer, reflux condenser, and gas addition tube is added 326.4 g of sodium acetate trihydrate and 81.6 g of glacial acetic acid diluted to 800 mL with water. To this acetate buffer solution is added 70.4 g of cyclopentanol. Adjacent to the flask is a 300 W tungsten lamp, and the remainder of the flask is wrapped with aluminum foil to reflect light. After addition of the cyclopentanol, the lamp is switched on and chlorine addition begins slowly through the gas addition tube. A total of 60 g of chlorine is added over a 60-minute period. Since the reaction liberates heat, chlorine feeding is temporarily suspended if the reaction temperature exceed 15 C. The reaction is complete after 0.5 hours. The reaction mixture is transferred to a 2000 mL separatory funnel and extracted into 200 mL of diethyl ether. The aqueous phase is discarded, and the ether phase is dried over MgSO4, filtered, and evaporated. The resultant product (90 g) is approximately 95% 5-chloropentanal and 5% unreacted cyclopentanal.

Reaction Step 2

To a nitrogen-purged 1000 mL 3-neck round-bottom pyrex glass flask fitted with a stirrer, reflux condenser, and 500 mL dropping funnel is added 3.2 g chiral catalyst DBNE in 50 g hexane and 24 g 5-chloropentanal at room temperature. The mixture is stirred for 20 minutes and and then cooled to 0 C. in an ice bath. 240 g of 2 Molar dimethyl zinc in toluene is added from a dropping funnel over a 30-minute period. The mixture is stirred for 16 hr at 0 C. The reaction is then quenched by adding 200 mL of 2 M HCl. The mixture is then extracted with 80 mL of methylene chloride.

The extract is dried over sodium sulfate, filtered, and evaporated. The resultant (R)-2-hydroxy-6-chlorohexane product is then added to a 1000- mL 3-neck flask with stirring and a condenser. 100 g of acetic anhydride are added via a dropping funnel, and the mixture is stirred at 60 C. for 2 hr. The (R1)-2-acetoxy-6-chlorohexane product is obtained by distillation of the reaction mixture under reduced pressure (B.P. 90 C. at 1 mm Hg). The final purity of that product is approximately 95% with an e.e. measured by optical rotation of 85%. The overall yield is 70%.

I claim:

1. A process for synthesizing a chiral secondary alcohol which comprises photohalogenating a cyclic alkanol to produce haloaldehyde and thereafter reacting said haloaldehyde with a dialkyl zinc in the presence of a chirally active catalyst to produce said chiral secondary alcohol.

2. A process as defined by claim 1 in which said cyclic alcohol has five to ten carbon atoms, said dialkyl zinc is dimethyl zinc, and said chirally active catalyst is a (1R,2S-C-1-N,N-dialkylnorephedrine) having 2 to 4 carbon atom alkyl groups.

3. A process for producing (R)-2-hydroxy-6-halohexane which consists essentially of the steps:
   (i) photohalogenating cyclopentanol to produce halopentanal, and (ii) reaching said halopentanal with dimethyl zinc in the presence of (1R,2S-C-1-N,N-dibutylnorephedrine) to produce (R)-6-halo-2-hexanol.

4. A process for producing (R)-2-acetoxy-6-chlorohexane which comprises:
   (i) photochloronating cyclopentanol to produce chloropentanal,
   (ii) reaching said chloropentanal with dimethyl zinc in the presence of (1R,2S-C-1-N,N-dibutylnorephedrine) to produce (R)-6-chloro-2-hexanol,
   (iii) acetylating said (R)-6-chloro-2-hexanol to produce (R)-2-acetoxy-6-chlorohexane, and
   (iv) recovering said (R)-2-acetoxy-6-chlorohexane product.

5. A process for producing (R)-2-acetoxy-6-bromohexane which comprises:
   (i) photobrominating cyclopentanol to produce bromopentanal,
   (ii) reaching said bromopentanal with dimethyl zinc in the presence of (1R,2S-C-1-N,N-dibutylnorephedrine) to produce (R)-6-bromo-2-hexanol,
   (iii) acetylating said (R)-6-bromo-2-hexanol to produce (R)-2-acetoxy-6-bromohexane, and
   (iv) recovering said (R)-2-acetoxy-6-bromohexane product.

* * * * *